United States Patent [19]

Leifheit et al.

[11] Patent Number: 5,126,070
[45] Date of Patent: Jun. 30, 1992

[54] CHLORINE DIOXIDE GENERATOR

[75] Inventors: David Leifheit; Richard Hutchings, both of Cincinnati, Ohio

[73] Assignee: The Drackett Company, Cincinnati, Ohio

[21] Appl. No.: 424,843

[22] Filed: Oct. 20, 1989

[51] Int. Cl.$^5$ .............................................. C01B 11/02
[52] U.S. Cl. ...................... 252/186.36; 252/186.37; 252/187.21; 252/187.23; 252/187.1
[58] Field of Search ............... 252/90, 187.23, 186.36; 206/219, 221, 484

[56] References Cited

U.S. PATENT DOCUMENTS

| | | | |
|---|---|---|---|
| 1,119,986 | 12/1914 | Pleger et al. | |
| 2,209,914 | 7/1940 | Gerber et al. | 128/272 |
| 2,409,084 | 10/1946 | Vincent | 127/71 |
| 2,482,891 | 9/1949 | Aston | 252/187 |
| 2,864,492 | 12/1958 | Lappala | 206/47 |
| 3,591,515 | 7/1971 | Lovely | 252/187.23 |
| 3,608,709 | 9/1971 | Pike | 206/47 A |
| 3,638,786 | 2/1972 | Borecki et al. | 252/90 |
| 3,741,805 | 6/1973 | Crotty et al. | 134/4 |
| 3,856,142 | 12/1974 | Vessalo | 206/530 |
| 4,084,747 | 4/1978 | Alliger | 252/187.23 |
| 4,104,190 | 8/1978 | Hartsborn | 252/187.23 |
| 4,145,001 | 3/1979 | Weyenberg et al. | 239/56 |
| 4,330,531 | 5/1982 | Alliger | 424/149 |
| 4,345,716 | 8/1982 | Armstrong et al. | 239/56 |
| 4,515,703 | 5/1985 | Hag | 252/90 |
| 4,534,509 | 8/1985 | Holzner | 239/34 |
| 4,547,381 | 10/1985 | Mason et al. | 426/316 |
| 4,585,482 | 4/1986 | Tice et al. | 252/187.23 |
| 4,689,169 | 8/1987 | Mason et al. | 252/186 |
| 4,731,193 | 3/1988 | Mason et al. | 252/95 |
| 4,762,124 | 8/1988 | Kerch et al. | 128/156 |
| 4,824,582 | 4/1989 | Nayer | 252/90 |
| 4,946,617 | 8/1990 | Sheridan et al. | 252/90 |

Primary Examiner—Richard D. Lovering
Assistant Examiner—Joseph D. Anthony
Attorney, Agent, or Firm—Charles J. Zeller; Doreen F. Shulman

[57] ABSTRACT

An article of manufacture comprising a rupturable pouch and an absorbent carrier for reacting a chlorite and an acid to form chlorine dioxide gas.

38 Claims, 1 Drawing Sheet

CHLORINE DIOXIDE GENERATOR

FIELD OF INVENTION

The present invention concerns means for reacting a chlorite and an acid to form chlorine dioxide gas.

BACKGROUND OF INVENTION

It is known that chlorine dioxide is formed by reaction of sodium chlorite and an acid. Thus, U.S. Pat. No. 3,591,515 to Lovely teaches the use of various acidifying agents to generate chlorine dioxide at a pH of less than 6. According to Lovely, a dry chlorine dioxide-yielding compound in powder form may be made by adsorbing a stabilized chlorine dioxide onto a basic-reacting adsorbent. The pulverized material is used to inhibit fungus growth in produce during shipment. U.S. Pat. No. 4,330,531 to Alliger discloses two-compartment containers for generating chlorine dioxide by reaction with an aqueous lactic acid solution. Thus, a syringe having two chambers separated by a common wall is shown, one chamber containing a sodium chlorite solution and the other chamber containing the lactic acid solution. Depressing the plunger simultaneously expels the solutions of each chamber. FIG. 4 in Alliger '531 illustrates a squeezable vial with two frangible containers therein, one container containing a sodium chlorite solution and the other containing a lactic acid solution. The vial has a cotton swab dauber in its outlet. FIG. 8 of '531 illustrates a plastic container crimped at about its midsection to form two chambers, one of which contains the chlorite solution and the other of which contains the acid solution. Removal of the crimp permits intermixing of the solutions.

U.S. Pat. No. 4,585,482 to Tice, et al. discloses a long-acting biocidal composition comprising a chlorine dioxide-liberating compound and sufficient hydrolyzable organic acid-generating polymer to lower the pH of the composition to less than about 7, the organic acid-generating polymer being present in a form whereby it is released gradually in the presence of water. The polymer is, for example, a methylvinylether/maleic anhydride copolymer.

None of the cited references disclose the formation of chlorine dioxide gas in a manner that takes advantage of its gaseous nature.

It has been found that the release of chlorine dioxide from its aqueous solution may be hastened and enhanced by generating the chlorine dioxide on an absorbent carrier. This allows the wicking action of the carrier to withdraw water from the aqueous system after the $ClO_2$ has been formed, following which the $ClO_2$ is emitted to the atmosphere.

It is an object of the present invention to provide an article of manufacture suitable to safely release chlorine dioxide to the atmosphere.

It is a primary object of the present invention to release chlorine dioxide by reacting a solution of sodium chlorite with an acid in dry form that has been impregnated into an absorbent carrier.

It is another object of this invention to provide chemical means in the absorbent carrier to accelerate the release of chlorine dioxide.

These and other objects and advantages of the present invention are set forth in the detailed description of the invention, a summary of which follows.

SUMMARY OF INVENTION

The article of manufacture of the present invention comprises a frangible pouch or other containment means for containing an aqueous chemical composition and absorbent carrier means for retaining one or more dry chemical constituents, said carrier means being exterior of and proximate to said pouch. Rupture of said pouch, for example, by squeezing, puncturing, etc., permits the aqueous chemical composition to be absorbed within said carrier and to then react with said one or more dry chemical compositions, to release chlorine dioxide.

In one embodiment, the rupturable or otherwise frangible pouch contains a solution of sodium chlorite, and the absorbent carrier retains a reactive material, e.g., an acid, in dry form capable of reacting with the sodium chlorite to form chlorine dioxide.

In another embodiment the carrier contains sodium chlorite or a chlorine dioxide forming material such as disclosed in the aforementioned Lovely patent, and an aqueous acid solution is contained in the rupturable pouch.

In a third embodiment, the frangible pouch may contain aqueous media not containing a reactant that participates in the formation of chlorine dioxide. Thus, the pouch may contain only water. The absorbent carrier, in this instance, would contain both the aforementioned dry reactant, e.g., the acid, and the sodium chlorite, also in dry form. These reactants would be proximate to one another, but preferably would not be touching one another.

In yet another embodiment, the article contains a carbonate which reacts with acid to form carbon dioxide, which gas assists in expelling the chlorine dioxide gas from the carrier.

DETAILED DESCRIPTION OF THE INVENTION

Chlorine dioxide is a strongly oxidizing gas that is quite soluble in water. As such, chlorine dioxide is a good bactericide and antiseptic.

Use of chlorine dioxide has not been widespread in general cleaning, disinfecting and deodorizing applications primarily because its form as a gas required in-situ generation and, especially, because once formed, its use is difficult to target. The rate of release of chlorine dioxide from the article of the present invention will vary with the nature of the use intended. When use as a general purpose cleaner with disinfection properties is intended, the article of the present invention provides a moderate rate of release of chlorine dioxide. When use as a deodorizer (i.e., odor eliminator) is intended, release should be faster, hastened possibly by incorporating a carbon dioxide-forming material, as hereinafter described. Thus, the article of the present invention is suitable to allow chlorine dioxide to be formed and used in a controlled manner.

Figure 1:
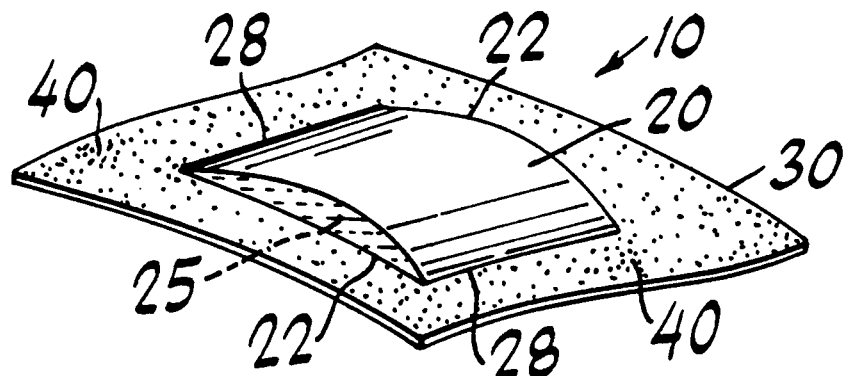
FIG. 1 is a perspective view of one embodiment of our invention.

One embodiment of the present invention is shown in FIG. 1. Thus, the article 10 comprises a pouch 20 for containing an aqueous solution 25. The pouch 20 is impervious to its contents, and is designed to burst upon application of pressure, as by squeezing. The pouch material must also not interact with the acid contained in the article 10 or the chlorine dioxide formed by its use. The pouch 20 may, for example, comprise two film layers 22 sealed at their peripheral edges 28. In such embodiment the seal between the two layers may be designed to rupture preferentially at the edges 28, whereby, in the article 10, the contents of the pouch 20 would be directed onto the substrate 30.

Suitable materials for the pouch 20 are polymeric films that are impervious to the chemical constituents present in the article. They include polyvinylidene chloride i.e Saran, polyvinyl chloride (PVC), polyolefins such as polyethylene and polypropylene, and polyethylene terephthalate, or other flexible film material laminates which have such films as their inner layer are also suitable.

The pouch 20 is affixed by any suitable means, for example, stitching, adhesive, thermal bonding, and the like, to an absorbent carrier 30 shown in FIG. 1 as a substrate. The substrate 30 may be a woven or nonwoven, synthetic or naturally, absorbent material or carrier. Suitable materials are cellulosic materials such as paper, cotton, sponge, meltblown, spunbonded and thermally bonded polyolefins including polyethylene and polypropylene, open-celled polyurethane, rayon, and blends of materials such as rayon and polypropylene fibers. The carrier 30 should be capable of absorbing virtually all of the aqueous solution 25. Typically, the carrier 30 will be able to absorb a quantity of solution equal to about 100% to 1000% of its own weight, preferably from about 4 to about 8 times its own weight. The substrate 30 is impregnated with a dry chemical substance 40 that is reactive with the aqueous solution 25 to form chlorine dioxide. Of course, the substrate 30 is generally resistant to the acid, the chlorite solution and the chlorine dioxide for at least the period use of the product.

In the preferred embodiment, the solution 25 contained in the pouch 20 is an alkali metal chlorite solution, preferably a sodium chlorite solution. The volume of the pouch 20 is typically about 0.5 to 50 ml, preferably 1 to 10 ml, most preferably 1 to 2 ml, of a 0.1% to 15% solution of sodium chlorite, preferably a 0.5% to 5% chlorite solution. (All concentrations are on a weight basis, unless otherwise noted.)

When the solution 25 is a chlorite solution, the dry chemical substance 40 is typically an acid. Any dry acid is suitable. Typically, the acid is present in the substrate 30 in an amount in excess over the stoichiometric amount needed to react with the chlorite. Illustrative are citric, succinic, sulfamic, maleic, oxalic, glutaric and other organic acids. Sodium bisulfate is suitable. Phosphoric acid adsorbed onto an amorphous silica powder is also suitable. Also suitable are other materials that react with sodium chlorite to form chlorine dioxide. Thus, compounds having acetal groups, for example, long chain carbohydrates and sugars, are suitable. Amines can also be used. Liquid acids of low volatility may also be adsorbed onto a carrier such as the amorphous silica. Generally, the dry reactant 40 is present in the carrier 30 at a level of from about 0.05 to about 5, preferably from about 0.1 to about 2, most preferably from about 0.2 to about 1.0 gram dry reactant per gram absorbent carrier. As used in this specification, the term "acid" and "acid solution" will also include other reactive species suitable for use in the present invention to react with the chlorite to form chlorine dioxide.

In another embodiment, the pouch 20 contains an acid solution, while the dry chemical substance 40 is sodium chlorite or other dry chlorine dioxide-producing material, for example, the "stabilized" chlorine dioxide disclosed in the aforementioned Lovely patent. In this embodiment, it should be understood that liquid acids in aqueous solution can be used, such as hydrochloric acid and acetic acid.

In yet another embodiment, the dry acid and the dry chlorite may each be impregnated onto the substrate 30, and the aqueous solution may be water. In this embodiment it is preferred that the acid and the chlorite be separately contained on the substrate 30. It is also preferred to have an area of acid-impregnated carrier alternate with an area of chlorite-containing carrier.

In still another embodiment, a carbon dioxide-generating material, such as an alkali metal carbonate or bicarbonate may be maintained in the article 10 in a nonreacting manner, until the device is activated. Thus, the carbonate may be in the aqueous chlorite solution or may be in the substrate 30 in dry form. The carbon dioxide helps expel the chlorine dioxide from the substrate. If sodium bicarbonate or other carbon dioxide producing agent is employed, the amount of acid in the pad should be sufficiently high to insure complete reaction of both the agent and the sodium chlorite.

The rate of release of the chlorine dioxide also may be regulated in other ways. Thus, the choice of acid will dictate whether the reaction proceeds rapidly or more slowly. Similarly, the concentration of the aqueous solution, as well as the absolute amount of water, will affect reaction rate. The choice of substrate 30 will also determine the rate of the reaction. Thus, the more the solution is wicked into the capillaries of the substrate, the drier will be the substrate, and the chlorine dioxide will be released more rapidly. Because the substrate 30 is capable of carrying moisture within its structure and without being saturated, this embodiment can be used as a disinfectant wipe, the wipe emitting chlorine dioxide gas during its use.

In another aspect of the present invention, a surface-active agent, typically a compatible anionic surfactant, may be incorporated, typically in the aqueous solution 25 in pouch 20. The surface-active agent is generally present in an amount of less than 5% by weight of the solution 25, preferably less than 2% by weight of the solution 25. When released into the carrier 30, the surface-active agent is available for cleaning, for example, by wiping surfaces to be cleaned with the article 10. The chlorine dioxide acts, in this instance, as a disinfectant for the hard surface. The surface active agent also assists in the wetting of the carrier 30, and helps distribute the aqueous solution.

Other optional components can be incorporated into the article 10. One such component is a buffer which will maintain the pH of the system above 9 thereby inhibiting spontaneous and unwanted production of chlorine dioxide. The addition of volatile alcohols which are miscible with the aqueous sodium chlorite solution will increase the evaporation rate of the chlorine dioxide and water from the carrier as well as the evolution rate of the carbon dioxide if generated. Any water soluble alkanol containing up to about four carbon atoms can be used for this purpose. Isopropyl alcohol is preferred.

The device 10 may be completely enclosed in an impervious foil wrapper to protect it during shipping. The foil wrapper (not shown) is discarded by the consumer, and may also be used to provide printed instructions for use of the article.

Figure 2:
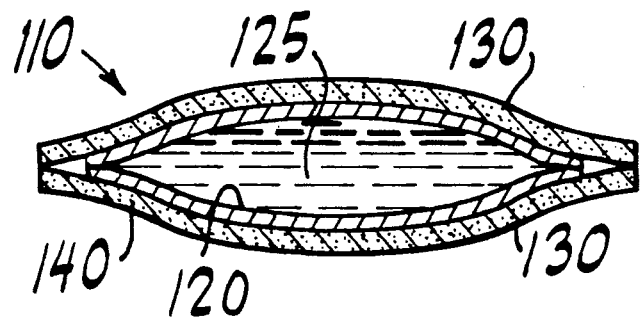
FIG. 2 is a sectional view of another embodiment of our invention.

Another embodiment is shown in FIG. 2, a cross-sectional view of the article. The article 110 shown in FIG. 2 is similar to the embodiment of FIG. 1, except that the pouch 120 containing the aqueous solution 125 is provided between a pair of substrates 130, thus providing a "sandwich" construction. The pouch 120 may be affixed to the substrates 130 by any suitable means, for example, by stitching, adhesive, thermal bonding, and the like.

As indicated above, the aqueous solution 125 may be chlorite solution, acid solution, or an aqueous solution not containing acid or chlorite. When the solution 125 is chlorite, the powder is the acid. When the pouch 120 contains the acid, the dry powder is the chlorite. Dry acid and dry chlorite are present on the substrate when the solution does not contain either of the above-identified reactants. The device 110 may also contain a surface-active agent, as in the case of the device 10.

The substrates 130 are made from the same materials as the substrate 30, and preferably are meltblown polypropylene fabrics or dry carded thermally bonded blends of rayon and polypropylene. In the preferred practice of this embodiment, a foil wrapping would enclose the entire article 110. The substrates 130 as well as the film layers comprising the pouch 120 may be heat-sealed, ultrasonically sealed, or radio frequency sealed. A heat-seal coating might be applied to the marginal areas, and then heated to effect a seal.

Figure 3:
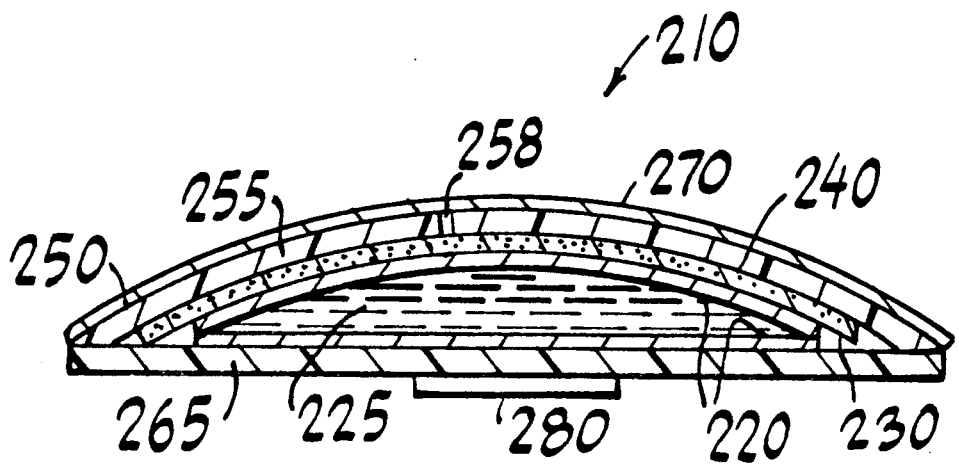
FIG. 3 is a sectional view of yet another embodiment of our invention.

A third embodiment is shown in FIG. 3, a cross-sectional view of article 210. In FIG. 3 the article 210 comprises an interior pouch 220, which is similar to that described in connection with the article 10. However, the pouch 220 is constructed so that it ruptures in the direction of substrate 230. The substrate 230 is in proximate association with the pouch 220, which substrate has been impregnated with a dry chemical substance 240, as previously indicated in respect of embodiments 10 and 110. The pouch 220-substrate 230 combination is retained within the two opposing substrates 255 and 265 comprising exterior compartment 250. Preferably, the substrate 255 is made of a liquid-impervious film material such as spun-bonded polypropylene nonwoven, and is provided with a plurality of apertures 258 for chlorine dioxide gas to escape. The number of apertures will determine how quickly the chlorine dioxide gas dissipates. In the embodiment shown, substrate 265 is merely a backing and does not contain apertures. In this embodiment, the flow of gas would be upward and radially away from substrate 255. Other materials disclosed in connection with the substrates 30 and 130 may be used for the substrates 255 and 230. In such instance the means for egress of gas from the interior of the compartment 250 may be the reticulations inherent in the structure of the material, that is, the porosity of the compartment. The porosity of the substrate 255 is typically from about 50 to about 250, preferably from about 100 to 200 Gurley units. Generally, the substrate 230 is more porous than the compartment substrates 255 and 265.

The compartment 250 may be sealed, for example, by a removable strip 270 adapted to cover the apertures 258. In this embodiment, means such as a peelable adhesive strip 280 or a hanger would be provided for use of the device as an odor eliminator.

EXAMPLE 1

An article similar to that shown in FIG. 2 was made. The outer compartment comprised two dry carded thermally bonded nonwovens that were sealed about their edges. The absorbent nonwovens were a blend of rayon, cotton and polypropylene fibers, and had a basis weight of 85 g/m$^2$. The fiber denier was 1.5, and provided a web sufficiently dense to retain a dry acid powder. The dry acid powder comprised phosphoric acid blended into amorphous silica. The powder was dry and free-flowing. Five grams were incorporated into the outer compartment.

An inner pouch of minimal headspace containing about 5 ml of a 2.5% aqueous sodium chlorite solution was contained within the interior of the outer pouch. The inner pouch was fabricated from 1.8 mil low-density polyethylene film.

The chlorite pouch was burst by finger pressure. The chlorite solution drained onto the acid powder, solubilized the acid, and initiated the formation of chlorine dioxide. The presence of chlorine dioxide gas was confirmed by collecting the resulting vapors in a gas trap and observing for the characteristic yellow color of chlorine dioxide. The gas release was rapid for the first 15 minutes.

EXAMPLE 2

This illustrates the embodiment of FIG. 3. The inner pouch had minimal headspace and contained 5 ml of a 5% sodium chlorite solution. The pouch was made of 1.8 mil low-density polyethylene film. A fibrous web of chemically bonded wood pulp airlay nonwoven was treated by immersing it into a 25% citric acid solution. The web was dried, the dried web containing 0.46 g citric acid per gram dry web. The web contained about 2.6 g citric acid, which amount was in excess of the stoichiometric amount needed to react with the sodium chlorite. An exterior compartment or pouch enclosed the inner pouch-web combination. The exterior pouch was made from spun-bonded polypropylene nonwoven and was provided with a plurality of openings. The porosity of the exterior compartment was 140 Gurley units.

The chlorite solution pouch was burst by finger pressure, causing the chlorite solution to run onto the acid-impregnated web. Chlorine dioxide was generated and built up in the exterior pouch until an equilibrium was reached between gas release, internal pouch pressure, and $ClO_2$ solubility. $ClO_2$ release was confirmed by detecting the characteristic odor of chlorine dioxide. The article 210 is suitable for use as an odor eliminator, wherein the chlorine dioxide oxidizes the malodor. Means to suspend or affix the device 210 in a confined space, e.g., a closet or room, would be provided.

What is claimed is:

1. An article of manufacture for generating and releasing chlorine dioxide gas at a controlled rate comprising a frangible pouch containing an aqueous solution of a dissolved reactant, an absorbent carrier for a dry reactant, and means for maintaining the pouch and the absorbent carrier in unitary association, whereby the aqueous solution is absorbed into the absorbent carrier when said pouch is broken, and the dissolved reactant reacts with said dry reactant to generate and release chlorine dioxide gas, and wherein the release rate of the chlorine dioxide gas can be controlled by the amount of dry reactant, the type of dry reactant, the concentration of the aqueous solution, the absolute amount of water, and the type of absorbent carrier.

2. The article of claim 1 wherein the dissolved reactant is sodium chlorite and the dry reactant is an acid.

3. The article of claim 1 wherein the dissolved reactant is an acid and the at least one dry reactant is sodium chlorite.

4. The article of claim 2 or 3 further comprising a reactant that reacts in aqueous media with said acid to generate carbon dioxide.

5. The article of claim 4 wherein the carbon dioxide-generating reactant is selected from the group sodium bicarbonate and sodium carbonate.

6. The article of claim 5 wherein the carbon dioxide-generating reactant is in the aqueous solution.

7. The article of claim 5 wherein the carbon dioxide-generating reactant is in a dry state and is present in the absorbent carrier.

8. The article of claim 2 or 3 wherein the acid is an organic acid.

9. The article of claim 8 wherein the organic acid is selected from the group consisting of oxalic, citric, lactic, maleic, glutaric, glycolic, sulfamic and succinic acids.

10. The article of claim 2 or 3 wherein the acid is selected from the group consisting of sodium bisulfate and liquid acids of low volatility adsorbed onto a pulverulent carrier therefor.

11. The article of claim 10 wherein the acid is phosphoric acid adsorbed onto an amorphous silica carrier.

12. An article of manufacture for generating and releasing chlorine dioxide gas at a controlled rate comprising a rupturable pouch containing an aqueous alkali metal chlorite solution, an absorbent carrier proximate to the pouch, a dry acid selected from the group consisting of organic acid, sodium bisulfate, and phosphoric acid adsorbed into the absorbent carrier, and means to retain the absorbent carrier proximate to the rupturable pouch, whereby the aqueous solution is absorbed by the absorbent carrier when the pouch is ruptured and the chlorite reacts with the acid to form and release chlorine dioxide gas, and wherein the release rate of the chlorine dioxide gas can be controlled by the amount of dry acid, the type of dry acid, the concentration of the aqueous alkali metal chlorite, solution, the absolute amount of water, and the type of absorbent carrier.

13. The article of claim 12 wherein the absorbent carrier is selected from the group consisting of natural and synthetic woven and nonwovens.

14. The article of claim 13 wherein the absorbent carrier can absorb a quantity aqueous solution equal to about 100% to about 1000% of its own weight.

15. The article of claim 14 wherein the absorbent carrier is selected from the group consisting of wet laid and air laid cellulose webs, rayon, sponge, polyurethane foams, cotton, polyolefin fibers and compatible combinations thereof.

16. The article of claim 15 wherein the absorbent carrier contains about 0.05 to about 5 gm acid per gram absorbent carrier.

17. The article of claim 12 or 16 wherein the pouch is made of an impervious film selected from the group consisting of polyvinylidene chloride, polyvinyl chloride, polyurethane, polyolefins, and polyethylene terephthalate.

18. The article of claim 2, 12 or 16 containing 0.5 to 50 ml of the chlorite solution which has a concentration of from about 0.1% to about 15%, by weight of the solution.

19. The article of claim 15 wherein the absorbent carrier further contains a carbon dioxide-generating agent.

20. An article of manufacture for generating and releasing chlorine dioxide gas at a controlled rate comprising an impervious, rupturable pouch containing an aqueous sodium chlorite solution having a concentration on a weight basis of from about 0.01% to about 15%;

a compartment enveloping the pouch, the compartment having chlorine dioxide gas outlet means;

an absorbent carrier between the pouch and the compartment, a dry acid selected from the group consisting of organic acid, sodium bisulfate, and phosphoric acid adsorbed onto the carrier, whereby the absorbent carrier absorbs the aqueous sodium chlorite solution when the pouch is ruptured, and the chlorite reacts with the acid to form gaseous chlorine dioxide, which is releasable through the chlorine dioxide gas outlet means.

21. The article of claim 20 wherein the chlorine dioxide gas outlet means is a plurality of apertures in an otherwise impermeable compartment.

22. The article of claim 20 wherein the chlorine dioxide gas outlet means is a permeable section of an otherwise impermeable compartment.

23. The article of claim 20 wherein the compartment comprises a pair of substrates, at least one of which is made from a gas-permeable, liquid-impermeable film selected from the group consisting of polyvinylidene chloride, polyvinyl chloride, polyurethane, polyolefins, and polyethylene terephthalate.

24. The article of claim 23 wherein the at least one substrate comprising the compartment has a porosity of from about 50 to about 250 Gurley units.

25. The article of claim 20 wherein the chlorine dioxide gas outlet means is the reticulations within the substrates comprising the compartment.

26. The article of claim 21 wherein the absorbent carrier is selected from the group consisting of wet laid and air laid cellulose webs, rayon, sponge polyurethane foams, cotton, polyolefin fibers and compatible combinations thereof, the absorbent carrier being more porous than the compartment.

27. The article of claim 25 wherein the carrier is capable of absorbing a quantity of aqueous solution equal to about 100% to 1000% of its own weight.

28. The article of claim 12 or 20 wherein the organic acid selected from the group consisting of sulfamic, succinic, oxalic, citric, lactic and maleic.

29. The article of claim 28 further comprising carbon dioxide-generating agents selected from the group consisting of sodium bicarbonate and sodium carbonate contained in the absorbent carrier, whereby carbon dioxide is also formed by reaction with the acid, when the pouch is ruptured.

30. The article of claim 28 further comprising a second absorbent carrier, said second absorbent carrier containing a carbon dioxide-generating agent.

31. An article of manufacture for generating and releasing chlorine dioxide gas at a controlled rate comprising a frangible pouch containing aqueous media, an absorbent carrier for sodium chlorite and an acid, and means for maintaining the pouch and the absorbent carrier in unitary association, whereby the aqueous media is absorbed into the absorbent carrier when the pouch is broken, and the sodium chlorite reacts with the acid to generate and release chlorine dioxide gas, and wherein the release rate of the chlorine dioxide gas can be controlled by the amount of sodium chlorite and acid, the type of acid, the concentration of the aqueous media, the absolute amount of water, and the type of absorbent carrier.

32. The article of claim 31 further comprising a carbon dioxide generating agent.

33. The article of claim 32 wherein the $CO_2$ generating agent is in the aqueous media.

34. The article of claim 1, 12, 20 and 31 further comprising closure means for the article in the form of an exterior impervious pouch.

35. The article of claim 12 or 20 further comprising means for suspending the article.

36. The article of claim 1, 12, 20 or 31 employed as a disinfectant wipe.

37. The article of claim 12 or 20 employed as an odor eliminator.

38. A method of using the article of claim 12 or 20 as an odor eliminator comprising commingling said article with clothes in the drum of a clothes dryer.

* * * * *